US012251688B2

United States Patent
Gawin et al.

(10) Patent No.: US 12,251,688 B2
(45) Date of Patent: *Mar. 18, 2025

(54) USE OF N-CHELATING RUTHENIUM COMPLEXES IN THE METATHESIS REACTION

(71) Applicant: Apeiron Synthesis S.A., Wroclaw (PL)

(72) Inventors: Rafal Gawin, Warsaw (PL); Patryk Krajczy, Glogowek (PL); Anna Gawin, Warsaw (PL); Krzysztof Skowerski, Jablonowo Pomorskie (PL)

(73) Assignee: Apeiron Synthesis S.A., Wroclaw (PL)

( * ) Notice: Subject to any disclaimer, the term of this patent is extended or adjusted under 35 U.S.C. 154(b) by 1057 days.

This patent is subject to a terminal disclaimer.

(21) Appl. No.: 17/051,209

(22) PCT Filed: Jul. 10, 2019

(86) PCT No.: PCT/IB2019/055864
§ 371 (c)(1),
(2) Date: Oct. 28, 2020

(87) PCT Pub. No.: WO2020/012370
PCT Pub. Date: Jan. 16, 2020

(65) Prior Publication Data
US 2021/0237045 A1    Aug. 5, 2021

(30) Foreign Application Priority Data
Jul. 12, 2018  (PL) ........................................ 426318

(51) Int. Cl.
| | |
|---|---|
| *B01J 31/22* | (2006.01) |
| *B01J 31/24* | (2006.01) |
| *C07C 67/333* | (2006.01) |
| *C07C 67/347* | (2006.01) |
| *C07F 15/00* | (2006.01) |

(52) U.S. Cl.
CPC ....... *B01J 31/2273* (2013.01); *B01J 31/2265* (2013.01); *B01J 31/2404* (2013.01); *C07C 67/333* (2013.01); *C07C 67/347* (2013.01); *C07F 15/0046* (2013.01); *B01J 2231/543* (2013.01); *B01J 2531/821* (2013.01)

(58) Field of Classification Search
CPC .......................... B01J 31/2278; B01J 31/2273
See application file for complete search history.

(56) References Cited

U.S. PATENT DOCUMENTS

| | | | | |
|---|---|---|---|---|
| 10,974,236 B2 * | 4/2021 | Skowerski | ........... | B01J 31/2278 |
| 11,192,911 B2 * | 12/2021 | Skowerski | ........... | B01J 31/2278 |
| 11,554,365 B2 * | 1/2023 | Gawin | ................ | C07D 207/02 |
| 2016/0075939 A1 * | 3/2016 | Afanasiev | ................ | C09K 8/80 |
| | | | | 507/224 |
| 2021/0101922 A1 * | 4/2021 | Gawin | ................ | B01J 31/1805 |
| 2023/0322830 A1 * | 10/2023 | Gawin | ................ | C07C 6/04 |
| | | | | 548/402 |

FOREIGN PATENT DOCUMENTS

| | | | |
|---|---|---|---|
| EP | 2452958 A1 | 5/2012 | |
| KR | 101553917 B1 | 9/2015 | |
| RU | 2462308 C1 * | 9/2012 | |
| RU | 2577252 C1 * | 3/2016 | |
| WO | 2011056881 A2 | 5/2011 | |
| WO | WO-2017185324 A1 * | 11/2017 | .......... B01J 31/1805 |

OTHER PUBLICATIONS

A Hoveyda et al., 450 Nature, 243-251 (2007) (Year: 2007).*
L. Delaude et al., 26 Kirk-Othmer Encyclopedia of Chemical Technology, 920-958 (2005) (Year: 2005).*
CAS Abstract and Indexed Compounds V. Afanasiev et al., US 2016/0075939 (2016) (Year: 2016).*
G. Yang et al., 566 Thermochimica Acta, 105-111 (2013) (Year: 2013).*
CAS Abstract and Indexed Catalyst Species K. Polyanskii et al., RU 2577252 (2016) (Year: 2016).*
Schaumann; Access to Skipped Polyene Macrolides through Ring-Closing Metathesis: Total Synthesis of the RNA Polymerase Inhibitor Ripostatin B; Angewandte Communications; 2012; Germany.
Seiser, et al.; Synthesis and Biological Activity of Largazole and Derivatives; Angewandte Communications; 2008; Switzerland.
Szadkowska, et al; Latent Thermo-Switchable Olefin Metathesis Initiators Bearing a Pyridyl-Functionalized Chelating Carbene: Influence of the Leaving Group's Rigidity on the Catalyst's Performance; Organometallics Article; 2010; Poland.
Zukowska, et al.; Thermal Switchability of N-Chelating Hoveyda-type Catalyst Containing a Secondary Amine Ligand; Organometallics; Poland; 2011.
Grubbs et al; Ruthenium-Based Heterocyclic Carbene-Coordinated Olefin Metathesis Catalysts; Institute of Physical Chemistry; 2010.
Stellfeld et al.; Synthesis of the A,B,C-Ring System of Hexacyclinic Acid; Organic Letters; 2004; Germany.
Tzur, et al.; Studies on Electronic Effects in O-, N- and S-Chelated Ruthenium Olefin-Metathesis Catalysts; Chemistry A European Journal; 2010; Germany.
Diesendruck, et al., Predicting the Cis-Trans Dichloro Configuration of Group 15-16 Chelated Ruthenium Olefin Metathesis Complexes: A DFT and Experimental Study; Inorganic Chemistry Article; 2009; Isreal.
Slugovc, et al.; Thermally Switchable Olefin Metathesis Initiators Bearing Chelating Carbenes: Influence of the Chelate's Ring Size; Organometallics, 2005; Austria.

(Continued)

*Primary Examiner* — Alexander R Pagano
(74) *Attorney, Agent, or Firm* — Dickinson Wright PLLC; Andrew D. Dorisio

(57) ABSTRACT

The subject matter of the invention is the use of a ruthenium complex of the formula 1, wherein the individual substituents have meanings as indicated in the olefin metathesis reactions description, including a reaction selected from such as ring-closing metathesis (RCM), homometathesis (self-CM) or cross metathesis (CM).

13 Claims, No Drawings

(56) References Cited

OTHER PUBLICATIONS

Nelson, et al.; Key Processes in Ruthenium-Catalysed Olefin Metathesis; ChemCom; Royal Society of Chemistry; 2014; United Kingdom.

Shu, et al.; RCM Macrocyclization Made Practical: an Efficient Synthesis of HCV Protease Inhibitor BILM 2061; Organic Letters; 2008; United States.

Hoefnagel, et al.; Substituent Effects. Basic Strength of Azatriptycene, Triphenylamine, and Some Related Amines; Laboratory of Organic Chemistry; 1981; Netherlands.

Polyanskii, K.B., et al.; Improved process for production of rutherium aminomethylbenzylidene chelate NHC complexes as catalysts for ring-opening metathetic polymerization; 2016; XP002795471.

Gawin; USPTO Office Action dated Aug. 30, 2023; U.S. Appl. No. 17/048,092.

\* cited by examiner

USE OF N-CHELATING RUTHENIUM COMPLEXES IN THE METATHESIS REACTION

FIELD OF THE INVENTION

The invention relates to the use of N-chelating ruthenium complexes of the general formula 1 as catalysts and/or (pre)catalysts in the olefin metathesis reaction.

BACKGROUND OF THE INVENTION

In recent years, significant progress has been made in application of olefin metathesis in organic synthesis [R. H. Grubbs (Editor), A. G. Wenzel (Editor), D. J. O'Leary (Editor), E. Khosravi (Editor), *Handbook of Olefin Metathesis, 2nd edition,* 3 vol. 2015, John Wiley & Sons, Inc., 1608 pages]. Many catalysts are known in the prior art that have both high activity in various types of metathesis reactions and high tolerance for functional groups. By combining these features, metathesis catalysts are important in modern organic synthesis and in industry. The most widely described (pre)catalysts in the literature are Grubbs, Hoveyda, indenylidene type complexes, and more recently Bertrand type catalysts having a carbene cycloalkylamine ligand (CAAC) [Grubbs et al. *Chem. Rev.* 2010, 110, 1746-1787; Nolan et al. *Chem. Commun.* 2014, 50, 10355-10375]. In other cases, most of the olefin metathesis catalyst structures are derived from the above-mentioned ruthenium complexes.

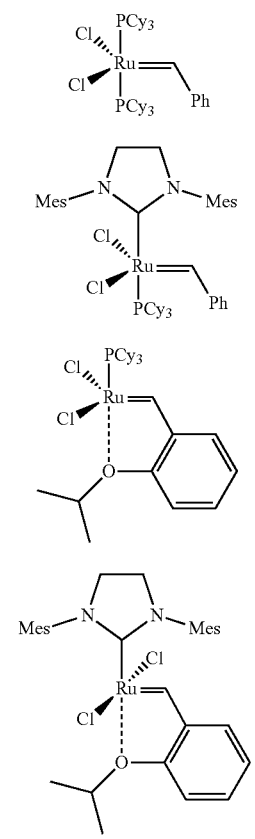

Gru-I

Gru-II

Hov-I

Hov-II

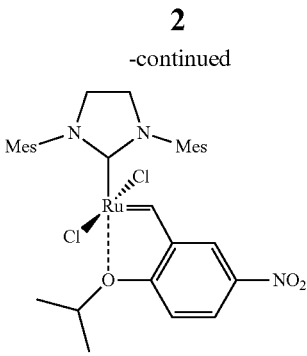

Gre-II

There are many examples of industrial applications of ruthenium complexes in which the use of fast initiating (pre)catalysts is preferred. The rate of initiation turned out to be crucial in the synthesis of natural compounds, an example being the application of Gre-II catalyst: Shu, C., Zeng, X., Hao, M.-H., Wei, X., Yee, N. K., Busacca, C. A., Han, Z., Farina, V., Senanayake, Ch. H., *Org. Lett.* 2008, 10, 1303-1306; Winter, P., Hiller, W., Christmann, M., *Angew. Chem. Int. Ed.* 2012, 51, 3396-3400; Stellfeld, T., Bhatt, U., Kalesse, M., *Org. Lett.* 2004, 6, 87; Seiser, T., Kamena, F., Cramer, N., *Ang. Chem. Int. Ed.* 2008, 47, 6483. Increasing the rate of Gre-II catalyst initiation was achieved by introduction an electron withdrawing nitro group [WO 2004/035596A1]. The nitro substituent decreases the electron density on the ether oxygen atom. As a consequence, the Ru—O bond is weakened, which makes the Gre-II complex a fast initiator of the metathesis reaction.

Many catalysts have been described in the prior art, the modifications of which were intended to affect (pre)catalyst activity by changing the electron density on a chelating heteroatom to ruthenium. Among these modifications, the benzylidene ligands having such atoms as: nitrogen, sulfur, selenium and phosphorus, which coordinate to ruthenium [Diesendruck, C. E., Tzur, E., Ben-Asuly, A., Goldberg, I., Straub, B. F., Lemcoff, N. G., *Inorg. Chem.* 2009, 48, 10819-10825], are described.

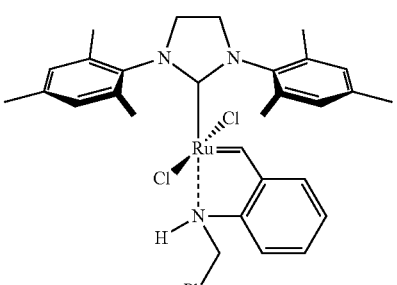

3

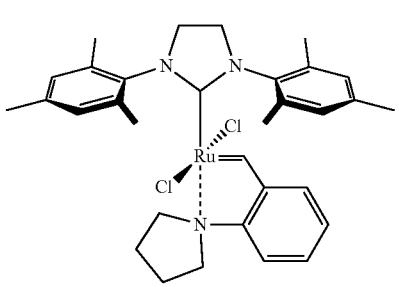

4

The most widely described are modifications in which the chelating oxygen atom has been replaced with nitrogen.

Slugovc described complexes having the Schiff base in the benzylidene ligand [Slugovc, C., Butscher, D., Stelzer, F, Mereiter, K., *Organometallics* 2005, 24, 2255-2258]. Grela presented the structure of the N-pyridine ligand complex [Szadkowska, A., Gstrein, X., Burtscher, D., Jarzembska, K., Woźniak, K., Slugovc, C., Grela, K., *Organometallics* 2010, 29, 117-124] and a series of complexes having a secondary amine in the benzylidene ligand (3) [Żukowska, K., Szadkowska, A., Pazio, A., Woźniak, K., Grela, K., *Organometallics* 2012, 31, 462-469]. Another example is a complex having a ligand with a chelating nitrogen atom which alkyl substituents together with the nitrogen atom form a pyrrolidine ring (4) [Tzur, E., Szadkowska, A., Ben-Asuly, A., Makal, A., Goldberg, I., Woźniak, K., Grela, K., Lemcoff, N. G., *Chem. Eur. J.* 2010, 16, 8726-8737]. The (pre)catalysts cited above are examples of latent N-chelating complexes requiring an elevated temperature or addition of an acid, e.g. Lewis acid for activation. Their latency is caused by the high electron density on the nitrogen atom, which is associated with the strong interaction of Ru—N and slow initiation.

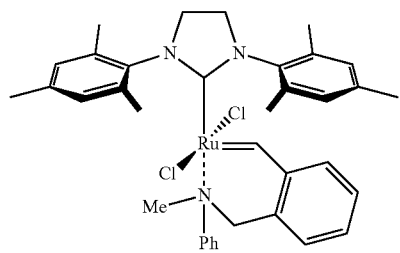

5

6a-f

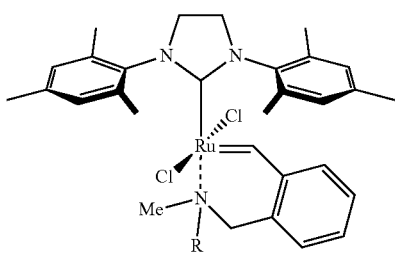

6a, R = Me
6b, R = Et
6c, R = CH$_2$CH$_2$OCH$_3$ 7a-c

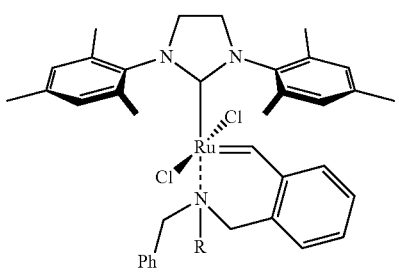

7a, R = CH$_2$Ph
7b, R = Me
7c, R = Et

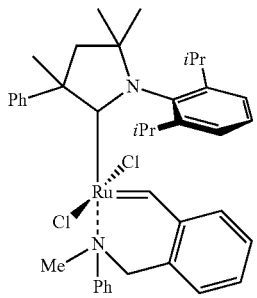

8

Also known in the prior art are latent N-heterocyclic (pre)catalysts having benzylidene ligands containing in the ortho position a group: —CH$_2$NR$_2$ or —CH$_2$NRR' (5-7). This group forms a six-membered chelating ring to the ruthenium atom. The properties (latency) of these complexes can also be explained by the high electron density at the nitrogen atom, resulting in a strong Ru—N interaction. These catalysts are described in patent applications WO 2017/185324 A1 (5), WO 2015/126279 A1 (6, 7) and a patent document RU 2462308 C1 (6, 7). Catalysts of this type are used as initiators of the ROMP reaction (EP 2452958 B1). In RU 2462308 C1 and WO 2015/126279 A1 7a-c complexes are described, as latent and useful in the DCPD metathesis polymerization reaction.

In addition, implementation of a cycloalkylamine carbene 8 (CAAC) in place of N-heterocyclic carbene is described (WO 2017/185324 A1). This catalyst was tested in the ethenolysis reaction and it was noted that even with this change requires chemical activation (addition of HSiCl$_3$).

The initiation rate of catalyst depends among others on the binding strength between Ru—N(or —Ru-another chelating heteroatom) in the benzylidene ligand. In the case of strong Ru—N interaction, the catalyst is initiating slowly (latent requires thermal or chemical activation) and is the most often used in ROMP reactions. In catalysts 5-8, a nitrogen atom (in the benzylidene ligand) strongly interacts with ruthenium. The electron density on the nitrogen atom is increased by alkyl substituents. The electron density can be correlated with the change of basicity in a series of differently substituted amines [Hoefnagel, A. J., Hoefnalgel, M. A., Wepster, B. M., *J. Org. Chem.* 1981 46, 4209-4211].

It has surprisingly been found that the (pre)catalysts represented by formula 1 are not latent catalysts but exhibit high activity in olefin metathesis reactions.

1

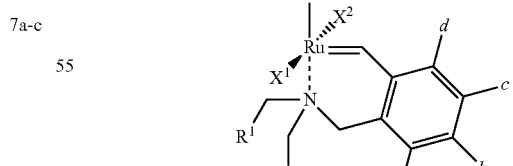

In the light of the prior art, it is not obvious that the catalyst of formula 1, which has at least one aryl substituent R$^1$ or R$^2$ in the benzylidene part, will have a high activity. This property is also contrary to the information contained in WO 2015/126279 A1. The introduction of an aryl group (R$^1$ and/or R$^2$), due to an insulating methylene group (between R¹ and/or R² and the nitrogen atom), does not significantly affect the reduction of the electron density on the nitrogen atom (as of the case with the latent (pre)catalysts known from the prior art (8)), which should consequently result in low (pre)catalyst 1 activity.

Complexes of formula 1 according to the invention are applicable in a wide range of reactions. Ring closing metathesis (RCM), cross metathesis (CM) and homometathesis (self-CM) can be performed with good results. (Pre)catalysts of the general Formula 1 in metathesis reactions show much higher activity than complexes having alkyl substituents on the nitrogen atom (Examples I-IV). The complexes of formula 1 used in a small amount catalyze reactions in a wide range of concentrations and temperatures, which greatly facilitates the development of an efficient process. The above-mentioned properties are desirable from the point of industrial application of ruthenium complexes as (pre)catalysts for the metathesis reaction.

SUMMARY OF THE INVENTION

Thus, the invention relates to the use of a compound represented by formula 1

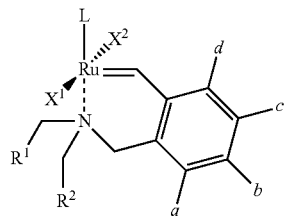

wherein:
$X^1$, $X^2$ independently represent an anionic ligand selected from such as a halogen atom, —OR, —SR, —C(C═O)R, where R represents $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, optionally $C_1$-$C_{12}$ perfluoroalkyl, optionally $C_1$-$C_{12}$ alkoxy, optionally a halogen atom;
$R^1$ represents a hydrogen atom or $C_5$-$C_{24}$ aryl, $C_1$-$C_{25}$ alkyl, $C_4$-$C_{25}$ heteroaryl, $C_7$-$C_{24}$ aralkyl, which are optionally substituted with at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups can be interconnected to form acyclic system;
$R^2$ represents $C_5$-$C_{24}$ aryl, $C_4$-$C_{25}$ heteroaryl, $C_7$-$C_{24}$ aralkyl, the groups being optionally substituted with at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups can be interconnected to form a cyclic system;
a, b, c, d independently represent a hydrogen atom, a halogen atom, $C_1$-$C_{25}$ alkyl, $C_1$-$C_{25}$ perfluoroalkyl, $C_3$-$C_7$ cycloalkyl, $C_1$-$C_{25}$ alkoxy, $C_5$-$C_{24}$ aryl, $C_7$-$C_{24}$ aralkyl, $C_5$-$C_{25}$ heteroaryl, 3 to 12-membered heterocycle, wherein the alkyl groups can be linked to each other to form a ring; may also independently represent an alkoxy (—OR'), thioether (—SR'), nitro (—NO₂), cyano (—CN), amide (—CONR'R'), carboxyl and ester (—COOR'), sulfonic (—SO₂R'), sulfonamide (—SO₂NR'R'), formyl and ketone (—COR') group, wherein R' and R" independently have the following meanings: $C_1$-$C_{25}$ alkyl, $C_1$-$C_{25}$ perfluoroalkyl, $C_5$-$C_{24}$ aryl, $C_5$-$C_{25}$ heteroaryl, $C_5$-$C_{24}$ perfluoroaryl;

L represents a neutral ligand, such as a $P(R')_3$ group, wherein R' independently represents $C_1$-$C_6$ alkyl, $C_3$-$C_8$ cycloalkyl, $C_5$-$C_{24}$ aryl, $C_7$-$C_{24}$ aralkyl, $C_5$-$C_{24}$ perfluoroaryl, two R' substituents can be linked to each other to form a cycloalkyl ring containing a phosphorus atom in the ring, or L is independently selected from the group including the so-called N-heterocyclic carbene ligands of formula 2a or 2b:

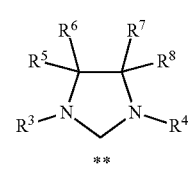

2a

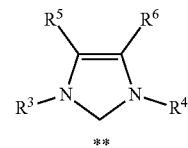

2b wherein:
each $R^3$ and $R^4$ independently represent $C_1$-$C_{12}$ alkyl, $C_3$-$C_{12}$ cycloalkyl, $C_5$-$C_{20}$ aryl, or $C_5$-$C_{20}$ heteroaryl, which is optionally substituted with at least one $C_1$-$C_{12}$ alkyl, $C_1$-$C_{12}$ perfluoroalkyl, $C_2$-$C_{12}$ alkoxy or a halogen atom;
each $R^5$, $R^6$, $R^7$, $R^8$, $R^9$, $R^{10}$ independently represent a hydrogen atom, $C_1$-$C_{12}$ alkyl, $C_3$-$C_{12}$ cycloalkyl, $C_5$-$C_{20}$ aryl, or $C_5$-$C_{20}$ heteroaryl, which is optionally substituted with at least one $C_1$-$C_{12}$ alkyl, $C_1$-$C_{12}$ perfluoroalkyl, $C_1$-$C_{12}$ alkoxy or a halogen atom, and $R^5$, $R^6$, $R^7$, $R^8$, $R^9$, $R^{10}$ groups may be optionally interconnected to form a $C_4$-$C_{10}$ cyclic or a policyclic $C_4$-$C_{12}$ system;
in olefin metathesis reactions including a reaction selected from such as ring-closing metathesis (RCM), homometathesis (self-CM) or cross-metathesis (CM).

Preferably, the compound is represented by formula 1

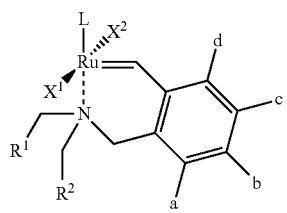

wherein:
$X^1$ and $X^2$ represent halogen atoms;
L represents a $P(R')_3$ group, wherein R' represents $C_3$-$C_8$ cycloalkyl or L represents a ligand of formula 2a or 2b, in which substituents $R^3$, $R^4$, $R^5$, $R^6$, $R^7$, $R^8$, $R^9$, $R^{10}$ have meanings as described above;
$R^1$ represents a hydrogen atom or $C_5$-$C_{24}$ aryl, $C_4$-$C_{25}$ heteroaryl, $C_7$-$C_{24}$ aralkyl, which are optionally substituted with at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups can be linked to each other to form a ring;

$R^2$ represents $C_5$-$C_{24}$ aryl, $C_4$-$C_{25}$ heteroaryl, which are optionally substituted with at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups can be interconnected to form a cyclic system;

a, b, c, d independently represent a hydrogen atom, an alkoxy (—OR'), thioether (—SR'), nitro (—NO$_2$), cyano (—CN), amide (—CONR'R'), carboxyl and ester (—COOR'), sulfone (—SO$_2$R'), sulfonamide (—SO$_2$NR'R'), formyl and ketone (—COR') group, in which the substituents R' and R" independently have the following meanings: $C_1$-$C_{25}$ alkyl, $C_1$-$C_{25}$ perfluoroalkyl, $C_5$-$C_{24}$ aryl, $C_5$-$C_{25}$ heteroaryl, $C_5$-$C_{24}$ perfluoroaryl.

Preferably, a compound is represented by formula 1

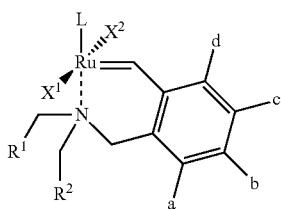

1 wherein $X^1$ and $X^2$ represent halogen atoms;

L represents P(R')$_3$ group, wherein R' represents $C_3$-$C_8$ cycloalkyl; or

L represents a ligand of formula 2a, wherein each $R^3$ and $R^4$ independently represent $C_1$-$C_{12}$ alkyl, $C_3$-$C_{12}$ cycloalkyl, $C_5$-$C_{20}$ aryl, which is optionally substituted with at least one $C_1$-$C_{12}$ alkyl, $C_1$-$C_{12}$ perfluoroalkyl, $C_2$-$C_{12}$ alkoxy, each $R^5$, $R^6$, $R^7$, $R^8$ independently represents a hydrogen atom, $C_1$-$C_{12}$ alkyl, $C_3$-$C_{12}$ cycloalkyl, $C_5$-$C_{20}$ aryl, or $C_5$-$C_{20}$ heteroaryl, which is optionally substituted with at least one $C_1$-$C_{12}$ alkyl, $C_1$-$C_{12}$ perfluoroalkyl, $C_1$-$C_{12}$ alkoxy or a halogen atom, and $R^5$, $R^6$, $R^7$, $R^8$ groups can optionally be interconnected to form a $C_4$-$C_{10}$ cyclic or $C_4$-$C_{12}$ polycyclic system;

$R^1$ represents a hydrogen atom or $C_5$-$C_{24}$ aryl, $C_4$-$C_{25}$ heteroaryl, which are optionally substituted with at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups can be interconnected to form acyclic system;

$R^2$ represents $C_5$-$C_{24}$ aryl, $C_4$-$C_{25}$ heteroaryl, which are optionally substituted with at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups can be interconnected to form acyclic system;

a, b, c, d independently represent a hydrogen atom, an alkoxy (—OR'), nitro (—NO$_2$), amide (—CONR'R'), ester (—COOR'), sulfone (—SO$_2$R'), sulfonamide (—SO$_2$NR'R') group, in which the substituents R' and R" independently have the following meanings: $C_1$-$C_{25}$ alkyl, $C_5$-$C_{24}$ aryl.

Preferably, a compound is represented by formula 1

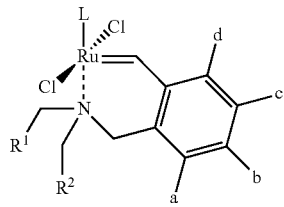

1 wherein

L represents P(R')$_3$ group, wherein R' represents $C_3$—C cycloalkyl; or

L represents a ligand of formula 2a, wherein each $R^3$ and $R^4$ independently represent $C_5$-$C_{20}$ aryl, which is optionally substituted with at least one $C_1$-$C_{12}$ alkyl, and each $R^5$, $R^6$, $R^7$, $R^8$ independently represents a hydrogen atom;

$R^1$ represents a hydrogen atom or $C_5$-$C_{24}$ aryl, $C_4$-$C_{24}$ heteroaryl, which are optionally substituted with at least one $C_1$-$C_{12}$ alkyl, optionally a halogen atom, wherein the alkyl groups can be interconnected to form acyclic system;

$R^2$ represents $C_5$-$C_{24}$ aryl or $C_4$-$C_{24}$ heteroaryl, which are optionally substituted with at least one $C_1$-$C_{12}$ alkyl, optionally a halogen atom, wherein the alkyl groups can be interconnected to form acyclic system;

a, b, c, d independently represent a hydrogen atom, an alkoxy group (—OR'), in which the substituent R' independently represents $C_1$-$C_{25}$ alkyl, $C_5$-$C_{24}$ aryl.

Preferably, a compound is represented by formula 1

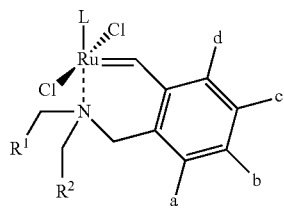

1 wherein

L represents tricyclohexylphosphine; or

L represents a ligand of formula 2a, in which each $R^3$ and $R^4$ independently represent $C_5$-$C_{20}$ aryl, which is optionally substituted with at least one $C_1$-$C_{12}$ alkyl, and each $R^5$, $R^6$, $R^7$, $R^8$ independently represent a hydrogen atom;

$R^1$ represents a hydrogen atom, $C_5$-$C_{24}$ aryl or $C_4$-$C_{25}$ heteroaryl, which are optionally substituted with at least one a halogen atom;

$R^2$ represents $C_5$-$C_{24}$ aryl or $C_4$-$C_{25}$ heteroaryl, which are optionally substituted with at least one halogen atom;

a, b, c, d independently represent a hydrogen atom, an alkoxy group (—OR'), wherein the substituent R' independently represents $C_1$-$C_{25}$ alkyl.

Preferably, the ruthenium compound of formula 1 has the structural formula selected from the following formulas 1a-1g;

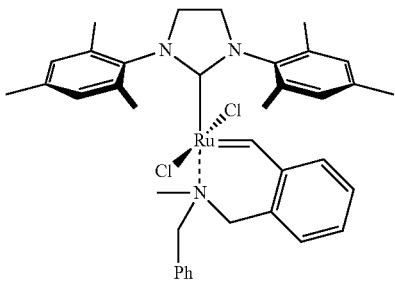

1a

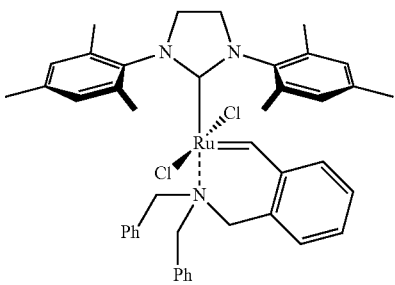

1b

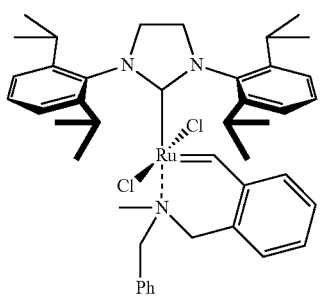

1c

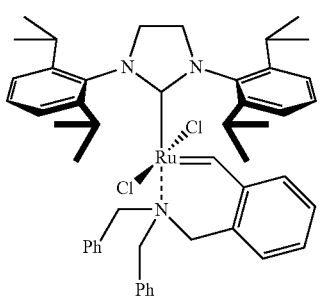

1d

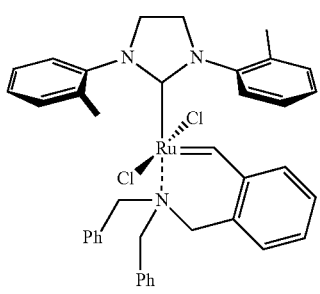

1e

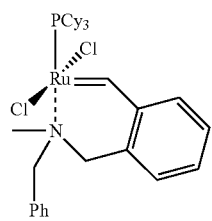

1f

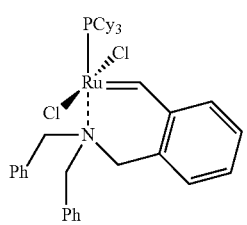

1g

Preferably, the reaction is carried out in an organic solvent such as toluene, benzene, mesitylene, dichloromethane, ethyl acetate, methyl acetate, tetrabutyl methyl ether, cyclopentyl methyl ether or without a solvent.

Preferably, the reaction is carried out at a temperature of from 0 to 150° C.

Preferably, the reaction is carried out at a temperature of from 20 to 120° C.

Preferably, the reaction is carried out from 1 minute to 24 hours.

Preferably, compound 1 is used in an amount not greater than 0.5 mol %.

Preferably, compound 1 is added to the reaction mixture in solid form and/or in the form of a solution in an organic solvent.

DETAILED DESCRIPTION

In the present description, the used terms have the following meanings. The undefined terms in this document have meanings that are given and understood by one of skill in the art in light of the best knowledge available, the present disclosure and the context of the description of the patent application. Unless otherwise stated, the following chemical terms conventions have been used in the present description that have the indicated meanings as in the definitions below:

As used herein, the term "halogen atom" represents an element selected from F, Cl, Br, I.

The term "carbene" represents a particle containing an inert carbon atom with a valence number of two and two unpaired valence electrons. The term "carbene" also includes carbene analogues in which the carbon atom is replaced with another chemical element such as boron, silicon, germanium, tin, lead, nitrogen, phosphorus, sulfur, selenium, tellurium.

The term "alkyl" refers to a saturated, linear, or branched hydrocarbon substituent with an indicated number of carbon atoms. Examples of alkyl substituent are -methyl, -ethyl, -n-propyl, -n-butyl, -n-pentyl, -n-hexyl, -n-heptyl, -n-octyl, -n-nonyl, and -n-decyl. Representative branched —(C1-C10)alkyles include -isopropyl, -sec-butyl, -isobutyl, -tert-butyl, -isopentyl, -neopentyl, -1-methylbutyl, -2-methylbutyl, -3-methylbutyl, -1, 1-dimethylpropyl, -1,2-dimethylpropyl, -1-methylpentyl, -2-methylpentyl, -3-methylpentyl, -4-methylpentyl, -1-ethylbutyl, -2-ethylbutyl, -3-ethylbutyl, -1,1-dimethylbutyl, -1,2-dimethylbutyl, -1,3-dimethylbutyl, -2,2-dimethylbutyl, -2,3-dimethylbutyl, -3,3-dimethylbutyl, -1-methylhexyl, -2-methylhexyl, -3-methylhexyl, -4-methylhexyl, -5-methylhexyl, -1,2-dimethylpentyl, -1,3-dimethylpentyl, -1,2-dimethylhexyl, -1,3-dimethylhexyl, -3,3-dimethylhexyl, -1,2-dimethylheptyl, -1,3-dimethylheptyl and -3,3-dimethylheptyl, and the like.

The term "alkoxy" refers to an alkyl substituent as defined above linked through an oxygen atom.

The term "perfluoroalkyl" represents an alkyl group as defined above in which all hydrogen atoms have been replaced by the same or different halogen atoms.

The term "cycloalkyl" refers to a saturated mono- or polycyclic hydrocarbon substituent with an indicated number of carbon atoms. Examples of the cycloalkyl substituent are -cyclopropyl, -cyclobutyl, -cyclopentyl, -cyclohexyl, -cycloheptyl, cyclooktyl, -cyclononyl, -cyclodecyl, and the like.

The term "alkenyl" refers to a saturated, linear, or branched non-cyclic hydrocarbon substituent having an indicated number of carbon atoms and containing at least one carbon-carbon double bond. Examples of the alkenyl substituent are -vinyl, -allyl, -1-butenyl, -2-butenyl, -isobutylenyl, -1-pentenyl, -2-pentenyl, -3-methyl-1-butenyl, -2-methyl-2-butenyl, -2,3-di-methyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

The term "aryl" refers to an aromatic mono- or polycyclic hydrocarbon substituent with an indicated number of carbon atoms. Examples of an aryl substituent are -phenyl, -tolyl, -silyl, -naphthyl, -2,4,6-trimethylphenyl, -2-fluorophenyl, -4-fluorophenyl, -2,4,6-trifluorophenyl, -2,6-difluorophenyl, -4-nitrophenyl and the like.

The term "aralkyl" refers to an alkyl substituent as defined above substituted with at least one aryl as defined above. Examples of aralkyl substituent are -benzyl, -diphenylmethyl, -triphenylmethyl and the like.

The term "heteroaryl" refers to an aromatic mono- or polycyclic hydrocarbon substituent with an indicated number of carbon atoms in which at least one carbon atom has been replaced by a heteroatom selected from O, N and S. Examples of a heteroaryl substituent are -furyl, -thienyl, -imidazolyl, -oxazolyl, -thiazolyl, -isoxazolyl, -triazolyl, -oxadiazolyl, -thiadiazolyl, -tetrazolyl, -pyridyl, -pyrimidyl, -triazinyl, -indolyl, -benzo[b]furyl, -benzo[b]thienyl, -indazolyl, -benzoimidazolyl, -azazolyl, -quinolyl, -isoquinolyl, -carbazolyl, and the like.

The term "heterocycle" refers to a saturated or partially unsaturated, mono- or polycyclic hydrocarbon substituent with an indicated number of carbon atoms in which at least one carbon atom has been replaced with a heteroatom selected from O, N and S. Examples of a heterocycle substituent are furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl, quinolinyl, isoquinolinyl, chromonyl, coumarinyl, indolyl, indolizinyl, benzo[b]furanyl, benzo[b]thiophenyl, indazolyl, purinyl, 4H-quinolizinyl, isoquinolyl, quinolyl, phthalazinyl, naphthyridinyl, carbazolyl, β-carbolinyl, and the like.

The term "neutral ligand" refers to a non-charged substituent capable of coordinating with a metallic center (a ruthenium atom). Examples of such ligands can be: amines, phosphines and their oxides, alkyl and aryl phosphites and phosphates, arsines and their oxides, ethers, alkyl and aryl sulphides, coordinated hydrocarbons, alkyl halides and aryl halides.

The term "anionic ligand" refers to a substituent capable of coordinating with a metallic center (a ruthenium atom) having a charge capable of partially or completely compensating the charge of the metallic center. Examples of such ligands may be fluoride anions, chloride, bromide, iodide, cyanide, cyanate and thiocyanate anions, carboxylic acid anions, alcohol anions, phenol anions, thiols and thiophene anions, hydrocarbon anions with delocalized charge (e.g. cyclopentadiene), anions of (organo)sulfuric and (organo) phosphoric acids and their esters (such as e.g. anions of alkylsulfonic and arylsulphonic acids, anions of alkylphosphoric and arylphosphoric acids, anions of alkyl and aryl esters of sulfuric acid, anions of esters of alkyl and aryl phosphoric acids, anions of alkyl and aryl esters of alkyl phosphorus and arylphosphoric acids). Optionally the anion ligand may have $L^1$, $L^2$ and $L^3$ groups, linked in the same way as the catechol anion, the acetylacetone anion, the salicylic aldehyde anion. Anion ligands ($X^1$, $X^2$) as well as neutral ligands ($L^1$, $L^2$, $L^3$) can be linked to each other to form multidentate ligands, e.g. a bidentate ligand ($X^1$-$X^2$), a tridential ligand ($X^1$-$X^2$-$L^1$), a tetradentate ligand ($X^1$-$X^2$-L-$L^2$), a bidentate ligand ($X^1$-$L^1$), a tridential ligand ($X^1$-$L^1$-$L^2$), a tetradentate ligand ($X^1$-L-$L^2$-$L^3$), a bidentate ligand ($L^1$-$L^2$), a tridential ligand ($L^1$-$L^2$-$L^3$). Examples of such ligands are: catechol anion, acetylacetone anion and salicylic aldehyde anions.

The term "heteroatom" represents an atom selected from the group of oxygen, sulfur, nitrogen, phosphorus and others.

EMBODIMENTS OF THE INVENTION

The following examples are only intended to illustrate the invention and to explain its particular aspects, without limitation, and should not be equated with its entire scope, which is defined in the appended claims. In the following examples, unless otherwise indicated, standard materials and methods used in the field were used or the manufacturers' recommendations for specific reagents and methods were followed.

The use of (pre)catalysts 1 was compared with (pre) catalysts C1-C3, structures of which are illustrated below:

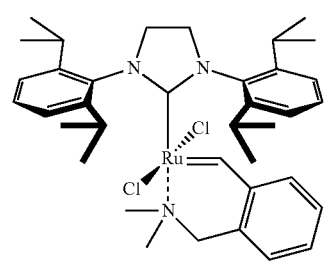

-continued

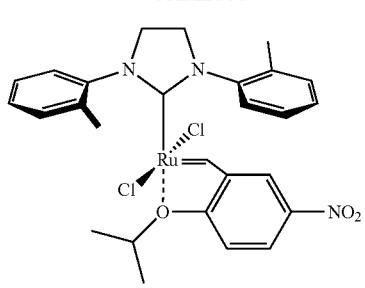

C3

Diethyl malonate (S1), ethyl undecenoate (S3), acrylonitrile and methyl stearate are commercially available compounds. Diethyl (2,2-dimethylallyl)malonate (S2) was prepared according to the procedure from literature, S1 and S3 were distilled under reduced pressure and stored over activated alumina. Acrylonitrile was dried with 4 Å molecular sieves and deoxygenated with argon. All reactions were carried out under argon. Toluene was washed with citric acid, water, dried with 4 Å molecular sieves and deoxidized with argon.

The composition of the reaction mixtures was examined by gas chromatography using a PerkinElmer Clarus 680 GC apparatus equipped with a GL Sciences InertCap 5 MS/NP capillary column.

The individual components of the reaction mixtures were identified by comparing the retention times with commercial standards or isolated from reaction mixtures for which the structure was confirmed by NMR.

Example I

Application Example: RCM Reaction of Diethyl Diallylmalonate (S1)

To a solution of S1 (0.240 g, 1.0 mmol) in toluene (10 ml) at a designated temperature a determined amount of the corresponding (pre)catalyst in toluene (50 μl) was added in one portion. At appropriate intervals, samples of the reaction mixture were taken, to which 3 drops of ethyl vinyl ether were added to deactivate the catalyst. The samples were analyzed by gas chromatography.

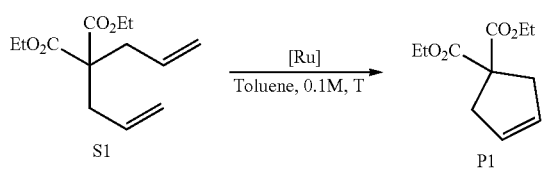

TABLE 1

Results of RCM reaction of diethyl diallylmalonate S1 at 29° C. using 0.1 mol % (pre)catalysts.

| Time [min] | Conversion [%] | |
| --- | --- | --- |
| | 1b | 1d |
| 2 | 41 | 30 |
| 5 | 72 | 63 |
| 10 | 91 | 90 |
| 20 | 98 | 99 |

TABLE 1-continued

Results of RCM reaction of diethyl diallylmalonate S1 at 29° C. using 0.1 mol % (pre)catalysts.

| Time [min] | Conversion [%] | |
| --- | --- | --- |
| | 1b | 1d |
| 30 | 99 | >99 |
| 60 | >99 | — |

TABLE 2

Results of RCM reaction of diethyl diallylmalonate S1 at 40° C. using 0.1 mol % (pre)catalysts.

| Time [min] | Conversion [%] | | | | |
| --- | --- | --- | --- | --- | --- |
| | C2 | 1a | 1b | 1c | 1d |
| 2 | — | — | 75 | — | 41 |
| 5 | — | — | 95 | — | 88 |
| 10 | — | — | >99 | — | 99 |
| 20 | — | — | — | — | >99 |
| 30 | — | — | — | — | — |
| 60 | <1 | 16 | — | 13 | — |

TABLE 3

Results of RCM reaction of diethyl diallylmalonate S1 at 80° C. using 0.1 mol % (pre)catalysts.

| Time [min] | Conversion [%] | | | | | | |
| --- | --- | --- | --- | --- | --- | --- | --- |
| | C2 | 1a | 1b | C1 | 1c | 1d | 1g |
| 2 | — | 20 | >99 | — | 13 | >99 | 34 |
| 5 | — | 51 | — | — | 18 | — | 66 |
| 10 | — | 77 | — | — | 30 | — | 90 |
| 20 | 13 | 88 | — | 19 | 43 | — | 99 |
| 30 | — | 91 | — | — | 47 | — | >99 |
| 60 | 24 | 94 | — | 33 | 52 | — | — |

Example II

Application Example: RCM Reaction of (2,2-Dimethylallyl) Malonate (S2)

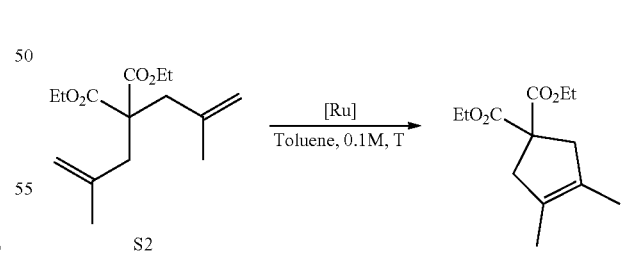

To a solution of S2 (0.240 g, 1.0 mmol) in toluene (10 ml) at a designated temperature a determined amount of the corresponding (pre)catalyst in toluene (50 μl) was added in one portion. At the appropriate time intervals, samples of the reaction mixture were taken, to which 3 drops of ethyl vinyl ether were added to deactivate the catalyst. The samples were analyzed by gas chromatography.

TABLE 4

Results of RCM reaction of (2,2-dimethylallyl) malonate (S2) at 80° C. using 0.5 mol % (pre)catalysts.

|  | Conversion [%] | |
| --- | --- | --- |
| Time [min] | C3 | 1e |
| 30 | 91 | 93 |
| 60 | 93 | 94 |

TABLE 5

Results of RCM reaction of (2,2-dimethylallyl) malonate (S2) at 100° C. using 0.5 mol % (pre)catalysts.

|  | Conversion [%] | |
| --- | --- | --- |
| Time [min] | C3 | 1e |
| 30 | 88 | 96 |
| 60 | 89 | 96 |

Example III

Application Example: RCM Reaction of Acrylonitrile with Ethyl Undecanoate (S3)

To a solution of S3 (1.062 g, 5.0 mmol, 1 molar equivalent), acrylonitrile (0.655 mL, 10.0 mmol, 2 molar equivalents) and methyl stearate (internal standard) in toluene (8.3 mL) at 85° C. under argon, a solution of the appropriate (pre)catalyst (100 ppm) in toluene (50 μl) was added in one portion. The reaction was stirred for 1 hour. A stream of argon was passed through the solution during the reaction. A sample was taken, into which 3 drops of ethyl vinyl ether were added to deactivate the catalyst. The sample was analyzed by gas chromatography.

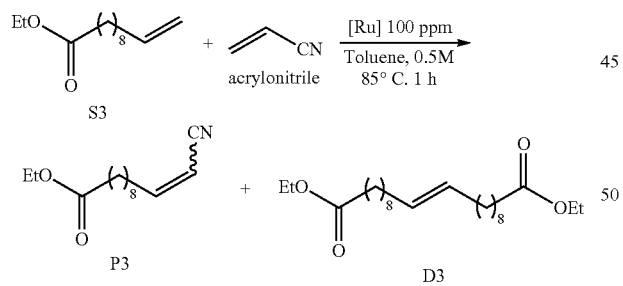

TABLE 6

Results of CM reaction of acrylonitrile with S3.

| (pre)catalyst [Ru] | Conversion [%] | P3 [%] | D3 [%] | Selectivity towards P3 [%] |
| --- | --- | --- | --- | --- |
| 1a | 34 | 32 | 2 | 94 |
| 1b | 26 | 24 | 2 | 92 |
| 1c | 55 | 46 | 9 | 84 |
| 1d | 44 | 37 | 7 | 84 |
| C2 | 17 | 16 | 1 | 94 |

Example IV

Application Example: Homometathesis of Ethyl Undecenoate (S3)

To S3 (3.00 g, 14.13 mmol) and methyl stearate (internal standard) at 85° C. under argon a solution of the appropriate (pre)catalyst (30 ppm) in toluene (50 μl) was added in one portion. The reaction was stirred for 1 hour. A stream of argon was passed through the solution during the reaction. A sample was taken, into which 3 drops of ethyl vinyl ether were added to deactivate the catalyst. The sample was analyzed by gas chromatography.

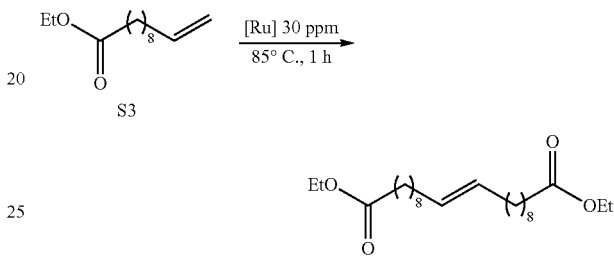

TABLE 7

Results of homodimerization reaction of S3.

| (pre)catalyst [Ru] | Conversion [%] | D3 [%] | Selectivity towards D3 [%] |
| --- | --- | --- | --- |
| 1a | 99 | 67 | 68 |
| 1b | 81 | 55 | 68 |
| 1c | 98 | 72 | 74 |
| 1d | 96 | 65 | 68 |
| C2 | 76 | 52 | 69 |
| C1 | 51 | 43 | 84 |

The C1-C2 (pre)catalysts known in the state of the art initiate the metathesis reaction of S3 without the addition of an activator, while their activity is significantly lower than (pre)catalysts 1a-d.

Example V

Synthesis of complex 1a.

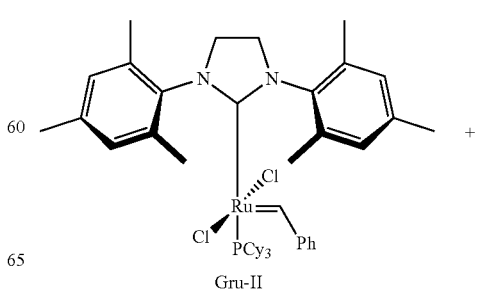

Gru-II

-continued

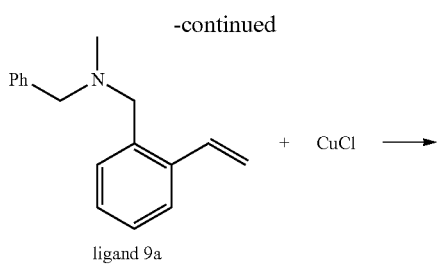

ligand 9a

1a

To the Gru-II complex (2.000 g, 2.36 mmol, 1 molar equivalent) dry deoxygenated toluene (23 ml), benzylidene ligand 9a (0.615 g, 2.59 mmol, 1.1 molar equivalent) and CuCl (0.350 g, 3.53 mmol, 1.2 molar equivalent) was added under argon. The reaction was stirred for 20 minutes at 55° C. Than was cooled to room temperature and concentrated to dryness. The residue was dissolved in ethyl acetate, filtered through a pad of Celite and concentrated to dryness. The crude product was isolated using column chromatography on silica gel (eluent:ethyl acetate/cyclohexane 2:98→1:9). The green fraction was collected and concentrated to dryness. The residue was dissolved in methylene chloride and excess of heptane was added. Methylene chloride was slowly removed under reduced pressure. The resulting precipitate was filtered and washed with cold heptane to give a green crystalline solid—(pre)catalyst 1a (1.340 g, 81%).

$^1$H NMR (CD$_2$Cl$_2$, 600 MHz): δ=18.70 (s, 1H), 7.50 (t. J=7.5 Hz. 1H), 7.31-7.23 (m, 3H), 7.19 (t, J=7.4 Hz. 1H), 7.05 (br s, 4H), 6.99 (br s, 2H), 6.90 (d, J=7.5 Hz, 1H), 6.74 (d, J=7.3 Hz, 1H), 4.10 (s, 4H), 3.90-3.00 (br m, 3H), 2.90-2.00 (br m, 19H), 1.73 (s, 3H).

$^{13}$C NMR (CD$_2$Cl$_2$, 150 MHz): δ=313.4, 313.3, 213.4, 148.9, 139.0, 134.0, 132.6, 132.5, 131.6, 129.8, 129.1, 129.0, 128.4, 128.3, 127.3, 60.0, 43.1, 32.4, 29.6, 23.3, 21.4, 14.4.

HRMS: ESI was calculated for C$_{37}$H$_{43}$N$_3$Ru [M-2Cl]$^{2+}$: 315.6250; found: 315.6247. (dimer)

Example VI

Synthesis of complex 1

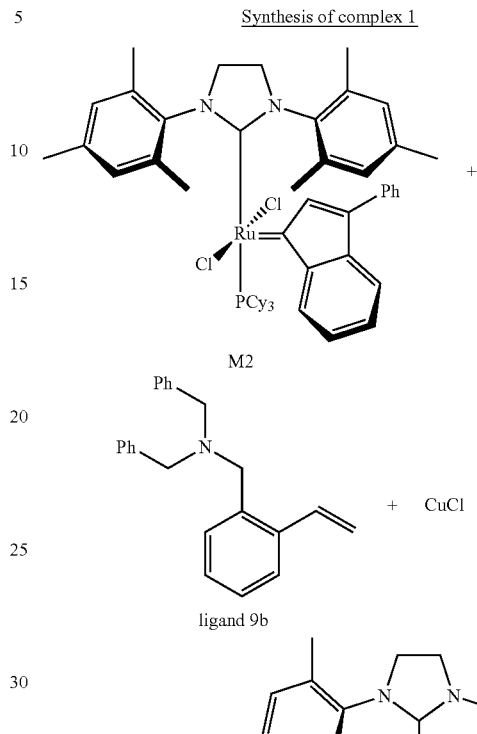

To the M2 complex (1.25 g, 2.36 mmol, 1 molar equivalent) dry deoxygenated toluene (13 ml), benzylidene ligand 9b (0.495 g, 1.58 mmol, 1.2 molar equivalent) and CuCl (0.183 g, 1.84 mmol, 1.4 molar equivalent) was added under argon. The reaction was stirred for 30 minutes at 70° C. Than was cooled to room temperature and concentrated to dryness. The residue was dissolved in ethyl acetate, filtered through a pad of Celite and concentrated to dryness. The crude product was isolated using column chromatography on silica gel (eluent:ethyl acetate/cyclohexane 2:98→1:9). The green fraction was collected and concentrated to dryness. The residue was dissolved in methylene chloride and excess of heptane was added. Methylene chloride was slowly removed under reduced pressure. The resulting precipitate was filtered and washed with cold heptane to give a green crystalline solid—(pre)catalyst 1b (0.490 g, 48%).

$^1$H NMR (CD$_2$Cl$_2$, 600 MHz): δ=18.61 (s, 1H), 7.60-6.30 (m, 18H), 4.60-1.50 (m, 28H).

$^{13}$C NMR (CD$_2$Cl$_2$, 150 MHz): δ=315.3, 213.2, 149.5, 139.0, 135.4, 134.6, 132.3, 131.0, 129.9, 129.1, 127.9, 127.8, 126.1, 58.8, 34.7, 22.9, 21.3, 14.4.

HRMS: ESI was calculated for C$_{43}$H$_{47}$N$_3$ClRu [M-Cl]$^+$: 742.2502; found: 742.2493.

Example VII

Synthesis of complex 1c

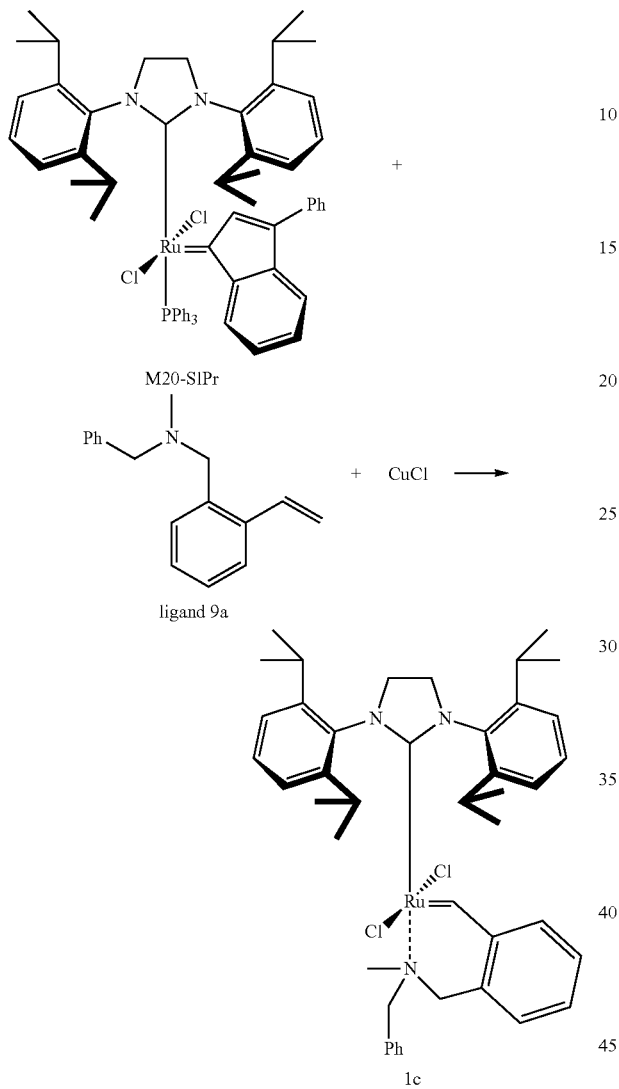

To the M20-SIPr complex (2.00 g, 1.97 mmol, 1 molar equivalent) dry deoxygenated toluene (19 ml), benzylidene ligand 9a (0.468 g, 1.97 mmol, 1.0 molar equivalent) and CuCl (0.293 g, 2.96 mmol, 1.5 molar equivalent) was added under argon. The reaction was stirred for 30 minutes at 80° C. Than was cooled to room temperature and concentrated to dryness. The residue was dissolved in ethyl acetate, filtered through a pad of Celite and concentrated to dryness. The crude product was isolated using column chromatography on silica gel (eluent:ethyl acetate/cyclohexane 2:98→1:9). The green fraction was collected and concentrated to dryness. The residue was dissolved in methylene chloride and excess of heptane was added. Methylene chloride was slowly removed under reduced pressure. The resulting precipitate was filtered and washed with cold heptane to give a green crystalline solid—(pre)catalyst 1c (0.470 g, 30%).

$^1$H NMR (CD$_2$Cl$_2$, 600 MHz): δ=18.61 (s, 1H), 7.70-6.70 (m, 14H), 6.57 (d, J=7.7 Hz, 1H), 4.80-2.30 (br m, 11H), 2.20-0.20 (br m, 28H).

$^{13}$C NMR (CD$_2$Cl$_2$, 150 MHz): δ=307.0, 215.5, 149.6, 148.1, 133.9, 132.7, 131.5, 129.9, 128.9, 128.7, 128.4, 128.3, 127.5, 124.9, 60.1, 55.1, 43.6, 29.2, 27.0, 23.9.

HRMS: ESI was calculated for C$_{45}$H$_{58}$N$_4$ClRu [M-Cl+CH$_3$CN]$^+$: 791.3397; found: 791.3391.

Example VIII

Synthesis of complex 1d

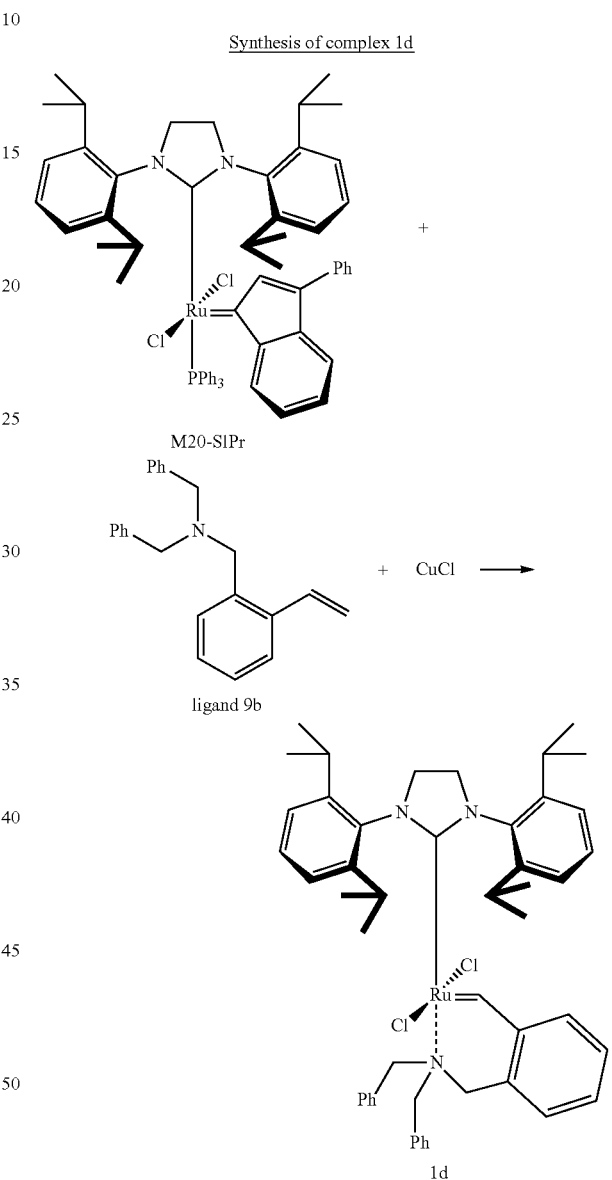

To the M20-SIPr complex (0.500 g, 0.49 mmol, 1 molar equivalent) dry deoxygenated toluene (5 mL), benzylidene ligand 9b (0.185 g, 0.59 mmol, 1.2 molar equivalent) and CuCl (0.059 g, 0.59 mmol, 1.2 molar equivalent) was added under argon. The reaction was stirred for 20 minutes at 60° C. It was cooled to room temperature and concentrated to dryness. The residue was dissolved in ethyl acetate, filtered through a pad of Celite and concentrated to dryness. The crude product was isolated using column chromatography on silica gel (eluent:ethyl acetate/cyclohexane 2:98→1:9). The green fraction was collected and concentrated to dryness. The residue was dissolved in methylene chloride and excess of heptane was added. Methylene chloride was slowly removed under reduced pressure. The resulting precipitate was filtered and washed with cold heptane to give a green crystalline solid—(pre)catalyst 1d (0.083 g, 20%).

$^1$H NMR (CD$_2$Cl$_2$, 600 MHz): δ=18.33 (s, 1H), 7.80-6.95 (m, 12H), 6.95-6.30 (m, 7H), 6.05 (d, J=7.7 Hz, 1H), 4.60-2.60 (br m, 14H), 2.0-0.20 (br m, 24H).

$^{13}$C NMR (CD$_2$Cl$_2$, 150 MHz): δ=311.0, 215.6, 148.6, 135.9, 132.8, 132.6, 130.0, 129.6, 128.6, 127.4, 127.4, 126.9, 126.4, 124.4, 62.2, 59.3, 57.4, 55.7, 32.4, 29.6, 27.8, 26.4, 23.7, 23.3, 14.4.

Example IX

Synthesis of complex 1e

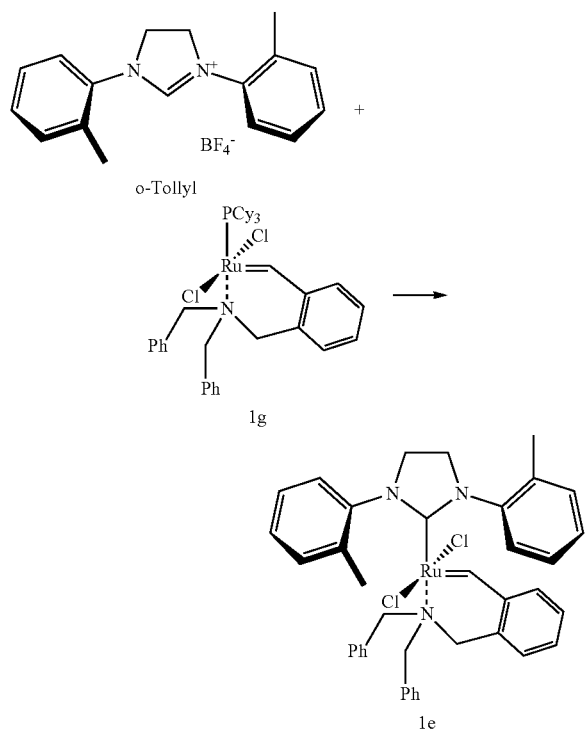

To the o-Tollyl compound (0.300 g, 1.04 mmol, 1.5 molar equivalent) dry deoxygenated toluene (5 mL) was added, placed in an oil bath heated to 45° C. and then LiHMDS (1 mL, 1.04 mmol, 1.5 molar equivalent) was added. After 5 minutes of reaction, 1g (0.522 g, 0.69 mmol, 1 molar equivalent) and CuCl (0.103 g, 1.04 mmol, 1.5 molar equivalent) were added under argon. The reaction was stirred for 20 minutes at 45° C. It was cooled to room temperature and concentrated to dryness. The residue was dissolved in ethyl acetate, filtered through a pad of Celite and concentrated to dryness. The crude product was isolated using column chromatography on silica gel (eluent:ethyl acetate/cyclohexane 2:98→1:9). The green fraction was collected and concentrated to dryness. The residue was dissolved in methylene chloride and excess of heptane was added. Methylene chloride was slowly removed under reduced pressure. The resulting precipitate was filtered and washed with cold heptane to give a green crystalline solid—(pre)catalyst 1e (0.274 g, 55%).

ESI was calculated for C$_{39}$H$_{39}$N$_3$ClRu [M-Cl]$^+$: 686.1878; found: 686.1884.

Synthesis of compound 1f

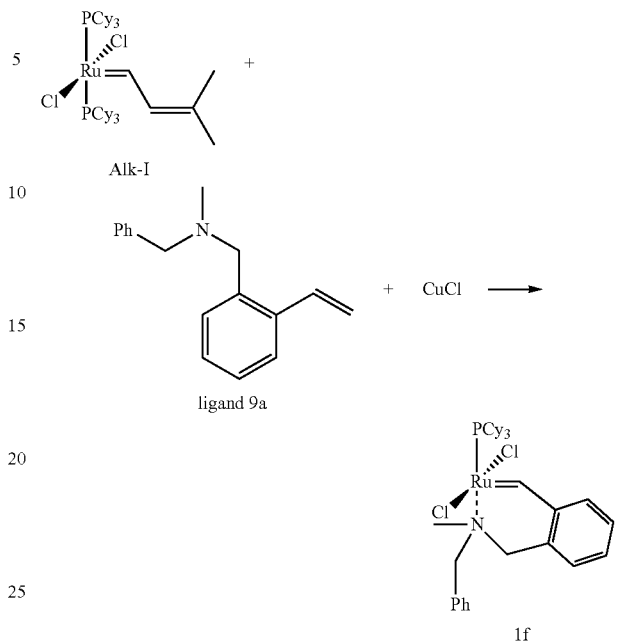

To the Alk-I complex (1.00 g, 1.25 mmol, 1 molar equivalent) dry deoxygenated methylene chloride (12 ml), benzylidene ligand 9a (0.356 g, 1.50 mmol, 1.2 molar equivalent) and CuCl (0.148 g, 1.50 mmol, 1.2 molar equivalent) was added under argon. The reaction was stirred for 20 minutes at 35° C. It was cooled to room temperature and concentrated to dryness. The residue was dissolved in ethyl acetate, filtered through a pad of Celite and concentrated to dryness. The residue was dissolved in methylene chloride and excess methanol was added. Methylene chloride was slowly removed under reduced pressure. The resulting precipitate was filtered and washed with cold methanol to give a green crystalline solid—(pre)catalyst 1f (0.592 g, 70%).

$^1$H NMR (CD$_2$Cl$_2$, 600 MHz): δ=19.15 (s, 1H), 7.90-6.70 (m, 9H), 4.45-4.05 (m, 2H), 2.40-2.26 (m, 3H), 2.12-1.90 (m, 8H), 1.88-1.58 (m, 16H), 1.36-1.16 (m, 11H).

$^{13}$C NMR (CD$_2$Cl$_2$, 150 MHz): δ=295.5, 148.2, 134.3, 133.2, 132.8, 132.4, 129.9, 129.1, 128.7, 128.6, 126.5, 63.1, 43.8, 35.2 (d, J=20.3 Hz), 30.7, 28.5 (d, J=10.0 Hz), 27.0, 26.9.

$^{31}$P NMR (CD$_2$Cl$_2$, 243 MHz): δ=35.6.

Example XI

Synthesis of compound 1g

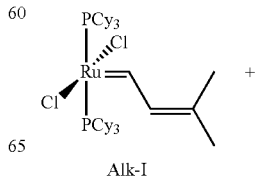

23

-continued

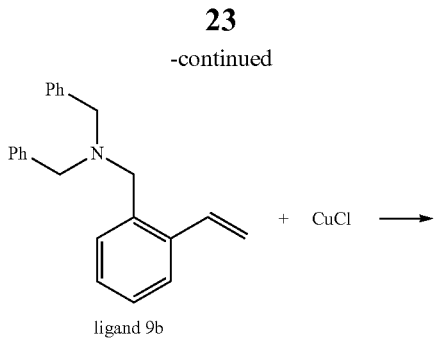

ligand 9b

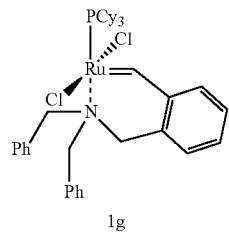

1g

To the Alk-I complex (1.00 g, 1.25 mmol, 1 molar equivalent) dry deoxygenated methylene chloride (12 ml), benzylidene ligand 9b (0.470 g, 1.50 mmol, 1.2 molar equivalent) and CuCl (0.148 g, 1.50 mmol, 1.2 molar equivalent) was added under argon. The reaction was stirred for 20 minutes at 35° C. It was cooled to room temperature and concentrated to dryness. The residue was dissolved in ethyl acetate, filtered through a pad of Celite and concentrated to dryness. The residue was dissolved in methylene chloride and excess methanol was added. Methylene chloride was slowly removed under reduced pressure. The resulting precipitate was filtered and washed with cold methanol to give a green crystalline solid—(pre)catalyst 1g (0.592 g, 63%).

$^1$H NMR (CD$_2$Cl$_2$, 600 MHz): δ=19.14 (d, J=10.2 Hz, 1H), 8.00-6.80 (m, 14H), 4.33 (d, J=14.0 Hz, 2H), 4.20-2.90 (br m, 2H), 2.39-2.26 (m, 3H), 2.05-1.60 (m, 22H), 1.38-1.16 (m, 10H).

$^{13}$C NMR (CD$_2$Cl$_2$, 150 MHz): δ=297.7, 148.9, 134.6, 133.0, 132.7, 129.6, 129.2, 128.6, 126.6, 60.2, 34.8 (d, J=20.3 Hz), 30.2, 28.5 (d, J=9.8 Hz), 27.0.

$^{31}$P NMR (CD$_2$Cl$_2$, 243 MHz): δ=34.5.

Example XII

Synthesis of ligand 9a

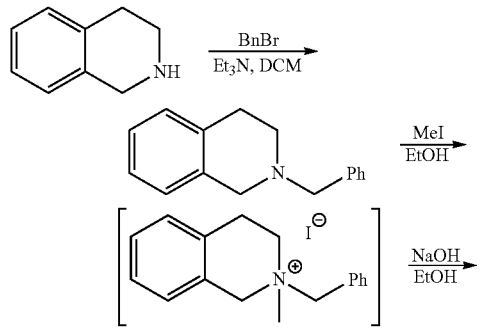

24

-continued

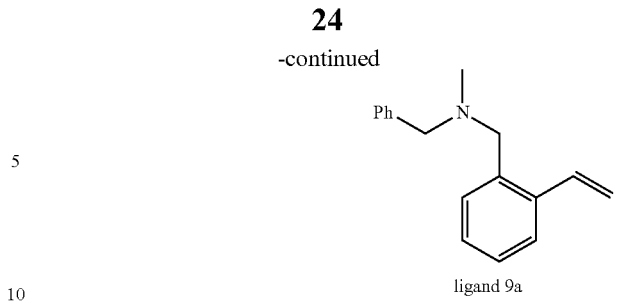

ligand 9a

To the solution of 1,2,3,4-tetrahydroisoquinoline (26.600 g, 200.0 mmol, 2 molar equivalents) and triethylamine (10.120 g, 100.0 mmol, 1 molar equivalent) in methylene chloride (500 ml) cooled to 0° C. benzyl bromide (17.100 g, 100.0 mmol, 1 molar equivalent) was added dropwise for 10 minutes. [The mixture] was slowly warmed to room temperature and stirred overnight. It was washed with water and dried over Na$_2$SO$_4$. It was filtered and evaporated. It was distilled under reduced pressure. The product was collected in a fraction with a boiling point of 126-132° C. at a pressure of 1.1×10−2 mbar (colorless oil, 18.470 g, 83%).

$^1$H NMR (CDCl$_3$, 600 MHz): δ=7.49-7.45 (m, 2H), 7.43-7.38 (m, 2H), 7.36-7.32 (m, 1H), 7.21-7.14 (m, 3H), 7.06-7.03 (m, 1H), 3.76 (s, 2H), 3.71 (s, 2H), 2.97 (t, J=5.9 Hz, 2H), 2.82 (t, J=5.9 Hz, 2H).

$^{13}$C NMR (CDCl$_3$, 150 MHz): δ=138.4, 134.9, 134.3, 129.0, 128.6, 128.2, 127.0, 126.5, 126.0, 125.5, 62.7, 56.1, 50.6, 29.3.

HRMS: ESI was calculated for C$_{16}$H$_{18}$N [M+H]$^+$: 224.1434; found: 224.1441.

To the amine, obtained in the previous step, (12.946 g, 58.0 mmol, 1 molar equivalent) in ethanol (96%, 150 ml) methyl iodide (16.460 g, 116.0 mmol, 2 molar equivalents) was added. It was stirred at 35° C. overnight. The excess of methyl iodide was evaporated under reduced pressure. NaOH (3.480 g, 87.0 mmol, 1.5 molar equivalents) was added. It was heated in reflux with condenser vigorously stirring overnight. It was cooled and concentrated to dryness. The residue was dissolved in methylene chloride, washed with water and dried over Na$_2$SO$_4$. Filtered and concentrate to dryness. The crude product was filtered through a thin pad of silica gel (eluent:ethyl acetate/cyclohexane 5:95). Concentrated to dryness to give a colorless oil—ligand 9a (12.711 g, 92%).

$^1$H NMR (CDCl$_3$, 600 MHz): δ=7.53 (dd, J=7.5; 1.6 Hz, 1H), 7.35-7.27 (m, 5H), 7.26-7.19 (m, 3H), 7.17 (dd, J=17.5; 10.9 Hz, 1H), 5.65 (dd, J=17.6; 1.5 Hz, 1H), 5.26 (dd, J=11.0; 1.5 Hz, 1H), 3.55 (s, 2H), 3.51 (s, 2H), 2.14 (s, 3H).

$^{13}$C NMR (CDCl$_3$, 150 MHz): δ=139.4, 137.7, 136.2, 134.9, 130.4, 129.0, 128.1, 127.3, 126.9, 125.6, 114.8, 62.1, 60.0, 42.0.

HRMS: ESI was calculated for C$_{17}$H$_{20}$N [M+H]$^+$: 238.1590; found: 238.1596.

Example XIII

Preparation of ligand 9b

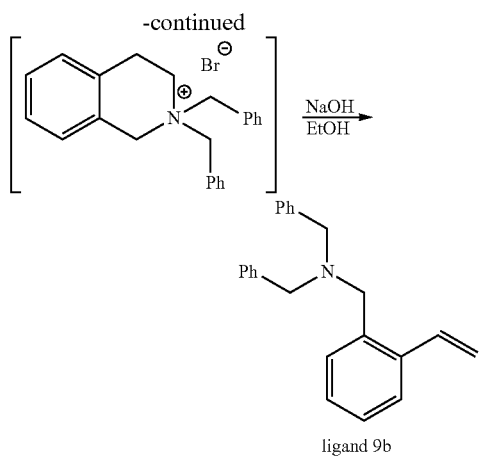

ligand 9b

To a solution of 1,2,3,4-tetrahydroisoquinoline (1.332 g, 10.0 mmol, 1 molar equivalent) and benzyl bromide (3.590 g, 21.0 mmol, 2.1 molar equivalents) in acetonitrile (100 mL) was added $K_2CO_3$ (2.073 g, 15.0 mmol, 1.5 molar equivalents). It was heated under reflux with condenser vigorously stirring for 4 hours. It was cooled, filtered and concentrated to dryness. The crude ammonium salt was dissolved in methylene chloride and excess ethyl acetate was added. Methylene chloride was slowly evaporated under reduced pressure. The precipitated product was filtered and washed with ethyl acetate. The ammonium salt was obtained as a white crystalline solid (3.880 g, 98%). The ammonium salt obtained in the previous step was dissolved in ethanol (96%, 50 ml) and NaOH (0.590 g, 14.8 mmol, 1.5 molar equivalent) was added. It was heated in reflux with stirring for 2 hours. The mixture was cooled and methanol was evaporated, yielding a yellow oil. It was dissolved in methylene chloride, washed with water. It was dried over $Na_2SO_4$, filtered and concentrated to dryness to give a slightly yellow oil (2.605 g, 84%).

$^1$H NMR (CDCl$_3$, 600 MHz): δ=7.56-7.52 (m, 1H), 7.50-7.46 (m, 1H), 7.43-7.39 (m, 4H), 7.38-7.34 (m, 4H), 7.31-7.25 (m, 4H), 7.05 (dd, J=17.4; 10.9 Hz, 1H), 5.64 (dd, J=17.4; 1.6 Hz, 1H), 5.25 (dd, J=10.9; 1.6 Hz, 1H), 3.64 (s, 2H), 3.57 (s, 4H).

$^{13}$C NMR (CDCl$_3$, 150 MHz): δ=139.4, 137.6, 136.4, 135.1, 130.3, 129.0, 128.1, 127.4, 127.2, 126.9, 125.6, 114.5, 58.2, 56.1, 26.9.

The invention claimed is:
1. A method comprising:
adding the ruthenium complex of formula 1 to a solution for an olefin metathesis reaction;

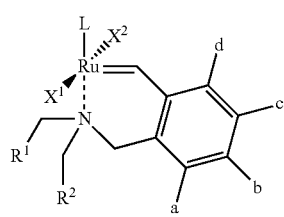

wherein:
the adding step includes using the ruthenium complex of formula 1 as a (pre)catalyst for a ring-closing metathesis reaction, homometathesis, or cross-metathesis;

$X^1$, $X^2$ are each independently an anionic ligand selected from a halogen atom, —OR, —SR, —C(C=O)R, where R is $C_1$-$C_{12}$ alkyl, $C_3$-$C_{12}$ cycloalkyl, $C_2$-$C_{12}$ alkenyl, $C_5$-$C_{20}$ aryl, which are optionally substituted with at least one $C_1$-$C_{12}$ alkyl, optionally $C_1$-$C_{12}$ perfluoroalkyl, optionally $C_1$-$C_{12}$ alkoxy, optionally a halogen atom;

$R^1$ represents $C_5$-$C_{24}$ aryl, $C_5$-$C_{25}$ heteroaryl, or $C_7$-$C_{24}$ aralkyl, which are optionally substituted by at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups may be linked to each other to form a ring;

$R^2$ represents $C_5$-$C_{24}$ aryl, $C_5$-$C_{25}$ heteroaryl, $C_7$-$C_{24}$ aralkyl, which are optionally substituted by at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups may be interconnected to form a cyclic system;

a, b, c, d are each independently a hydrogen atom, a halogen atom, $C_1$-$C_{25}$ alkyl, $C_1$-$C_{25}$ perfluoroalkyl, $C_3$-$C_7$ cycloalkyl, $C_1$-$C_{25}$ alkoxy, $C_5$-$C_{24}$ aryl, $C_7$-$C_{24}$ aralkyl, $C_5$-$C_{25}$ heteroaryl, 3-12-membered heterocycle, wherein the alkyl groups can be linked to each other to form a ring, wherein a, b, c, d can each also be independently an alkoxy group (—OR'), thioether (—SR'), nitro (—NO2), cyano (—CN), amide (—CONR'R"), carboxyl and ester (—COOR'), sulfone (—SO2R'), sulfonamide (SO2NR'R"), formyl and ketone (—COR'), in which the substituents R' and R" independently have the following meanings: $C_1$-$C_{25}$ alkyl, $C_1$-$C_{25}$ perfluoroalkyl, $C_5$-$C_{24}$ aryl, $C_5$-$C_{25}$ heteroaryl, $C_5$-$C_{24}$ perfluoroaryl;

L represents a neutral ligand, wherein the neutral ligand comprises a P(R')$_3$ group, in which R' independently represents $C_1$-$C_6$ alkyl, $C_3$-$C_8$ cycloalkyl, $C_5$-$C_{24}$ aryl, $C_1$-$C_{24}$ aralkyl, $C_5$-$C_{24}$ perfluoroaryl, two substituents R' can be interconnected to form a cycloalkyl ring containing a phosphorus atom in the ring, or L is selected independently from the group consisting of N-heterocyclic carbene ligands of the formula 2a or 2b:

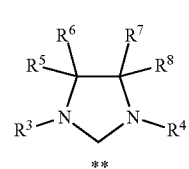

2a

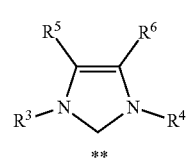

2b wherein each $R^3$ and $R^4$ independently represent $C_1$-$C_{12}$ alkyl, $C_3$-$C_{12}$ cycloalkyl, $C_5$-$C_{20}$ aryl, or $C_5$-$C_{20}$ heteroaryl, which is optionally substituted with at least one $C_1$-$C_{12}$ perfluoroalkyl, $C_2$-$C_{12}$ alkoxy or a halogen atom, wherein the $C_5$-$C_{20}$ aryl is formulas 3a or 3b; and

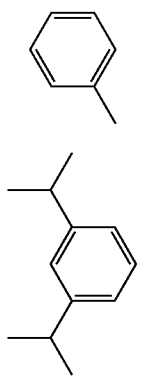

wherein each $R^5$, $R^6$, $R^7$, $R^8$ independently represents a hydrogen atom, $C_1$-$C_{12}$ alkyl, $C_3$-$C_{12}$ cycloalkyl, $C_5$-$C_{20}$ aryl, or $C_5$-$C_{20}$ heteroaryl, which is optionally substituted with at least one $C_1$-$C_{12}$ alkyl, $C_1$-$C_{12}$ perfluoroalkyl, $C_2$-$C_{12}$ alkoxy or a halogen atom, and the $R^5$, $R^6$, $R^7$, $R^8$, groups can be optionally interconnected to form a $C_4$-$C_{10}$ cyclic or $C_4$-$C_{12}$ polycyclic system.

2. The method of claim 1, wherein in the ruthenium complex of formula 1

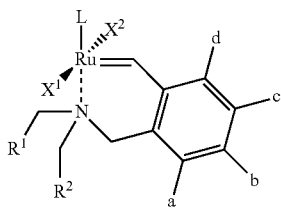

$X^1$ and $X^2$ represent halogen atoms;

L represents a $P(R')_3$ group, wherein R' represents $C_3$-$C_8$ cycloalkyl, or L represents a ligand of formula 2a or 2b, in which substituents $R^3$, $R^4$, $R^5$, $R^6$, $R^7$, $R^8$ are as defined above;

$R^1$ represents $C_5$-$C_{24}$ aryl, $C_4$-$C_{25}$ heteroaryl, or $C_1$-$C_{24}$ aralkyl, which are optionally substituted with at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups can be interconnected to form a cyclic system;

$R^2$ represents $C_5$-$C_{24}$ aryl, $C_4$-$C_{25}$ heteroaryl, which are optionally substituted with at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups can be linked to each other to form a ring; and a, b, c, d independently represent a hydrogen atom, an alkoxy (—OR'), thioether (—SR'), nitro (—NO2), cyano (—CN), amide (—CONR'R"), carboxyl and ester (—COOR'), sulfone (—SO2R'), sulfonamide (—SO2NR'R"), formyl and ketone (—COR') group, where the substituents R' and R" independently have the following meanings: $C_1$-$C_{25}$ alkyl, $C_1$-$C_{25}$ perfluoroalkyl, $C_5$-$C_{24}$ aryl, $C_5$-$C_{25}$ heteroaryl, $C_5$-$C_{24}$ perfluoroaryl.

3. The method of claim 1, wherein in the ruthenium complex of formula 1

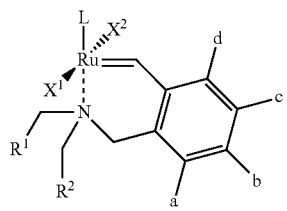

$X^1$ and $X^2$ represent halogen atoms;

L represents a $P(R')_3$ group, in which R' represents $C_3$-$C_8$ cycloalkyl, or L represents a ligand of formula 2a, in which each $R^3$ and $R^4$ independently represent $C_1$-$C_{12}$ alkyl, $C_3$-$C_{12}$ cycloalkyl, or $C_5$-$C_{20}$ aryl, which is optionally substituted with at least one $C_1$-$C_{12}$ perfluoroalkyl, or $C_2$-$C_{12}$ alkoxy, wherein the $C_5$-$C_{20}$ aryl is formula 3a or formula 3b, and each $R^5$, $R^6$, $R^7$, $R^8$ independently represents a hydrogen atom, $C_1$-$C_{12}$ alkyl, $C_3$-$C_{12}$ cycloalkyl, $C_5$-$C_{20}$ aryl, or $C_5$-$C_{20}$ heteroaryl, which is optionally substituted with at least one $C_1$-$C_{12}$ alkyl, $C_1$-$C_{12}$ perfluoroalkyl, $C_2$-$C_{12}$ alkoxy or a halogen atom, and the $R^5$, $R^6$, $R^7$, $R^8$ groups can be optionally interconnected to form a $C_4$-$C_{10}$ cyclic or $C_4$-$C_{12}$ polycyclic system;

$R^1$ represents $C_5$-$C_{24}$ aryl, or $C_4$-$C_{25}$ heteroaryl, which are optionally substituted with at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups can be interconnected to form a cyclic system;

$R^2$ represents $C_5$-$C_{24}$ aryl, $C_4$-$C_{25}$ heteroaryl, which are optionally substituted with at least one $C_1$-$C_{12}$ alkyl, optionally $C_1$-$C_{12}$ perfluoroalkyl, optionally $C_1$-$C_{12}$ alkoxy, optionally a halogen atom, wherein the alkyl groups can be interconnected to form acyclic system;

a, b, c, d independently represent a hydrogen atom, an alkoxy (—OR'), nitro (—NO2), amide (—CONR'R"), ester (—COOR'), sulfone (—SO2R'), sulfonamide (—SO2NR'R") group, in which the substituents R' and R" independently have the following meanings: $C_1$-$C_{25}$ alkyl, $C_5$-$C_{24}$ aryl.

4. The method of claim 1, wherein in the ruthenium complex of formula 1

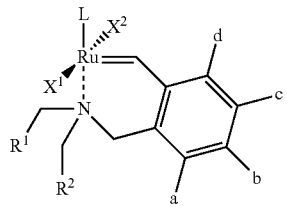

L represents a $P(R')_3$ group, in which R' represents $C_3$-$C_8$ cycloalkyl, or L represents a ligand of formula 2a, in which each $R^3$ and $R^4$ independently represent $C_5$-$C_{20}$ aryl, wherein the $C_5$-$C_{20}$ aryl is formulas 3a or 3b, and each $R^5$, $R^6$, $R^7$, $R^8$ independently represents a hydrogen atom;

$R^1$ represents $C_5$-$C_{24}$ aryl, or $C_4$-$C_{24}$ heteroaryl, which are optionally substituted with at least one $C_1$-$C_{12}$ alkyl, optionally a halogen atom, wherein the alkyl groups can be interconnected to form a cyclic system;

$R^2$ represents $C_5$-$C_{24}$ aryl or $C_4$-$C_{24}$ heteroaryl, which are optionally substituted with at least one $C_1$-$C_{12}$ alkyl, optionally a halogen atom, wherein the alkyl groups can be interconnected to form a cyclic system;

a, b, c, d independently represent a hydrogen atom, or an alkoxy group (—OR'), in which the substituent R' independently represents $C_1$-$C_{25}$ alkyl, or $C_5$-$C_{24}$ aryl.

5. The method of claim 1, wherein in the ruthenium complex of formula 1

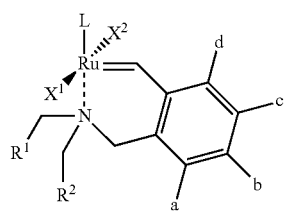

1

L represents tricyclohexylphosphine, or

L represents a ligand of formula 2a, in which each $R^3$ and $R^4$ independently represent $C_5$-$C_{20}$ aryl, wherein the $C_5$-$C_{20}$ aryl is formulas 3a or 3b, and each $R^5$, $R^6$, $R^7$, $R^8$ independently represents a hydrogen atom;

$R^1$ represents $C_5$-$C_{24}$ aryl or $C_4$-$C_{25}$ heteroaryl, which are optionally substituted with at least one a halogen atom;

$R^2$ represents $C_5$-$C_{24}$ aryl or $C_4$-$C_{25}$ heteroaryl, which are optionally substituted with at least one a halogen atom;

a, b, c, d independently represent a hydrogen atom, or an alkoxy group (—OR'), in which the substituent R' independently represents $C_1$-$C_{25}$ alkyl.

6. The method of claim 1, wherein ruthenium complex of formula 1 has a structure represented by a structural formula selected from the formulas 1d, 1e, and 1g.

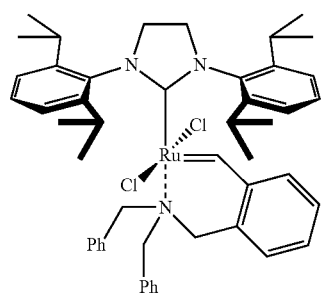

1d

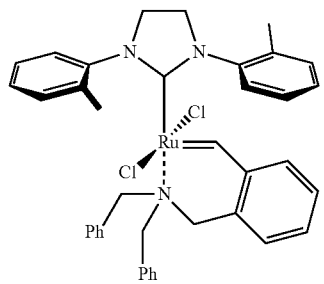

1e

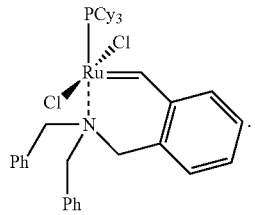

1g

7. The method of claim 1 wherein the adding step includes an organic solvent, wherein the organic solvent includes toluene, benzene, mesitylene, dichloromethane, ethyl acetate, methyl acetate, tetrabutyl methyl ether, or cyclopentyl methyl ether.

8. The method of claim 1 wherein the adding step includes conducting the olefin metathesis reaction at a temperature of from 0 to 150° C.

9. The method of claim 8 wherein the adding step includes conducting the olefin metathesis reaction at a temperature of from 20 to 120° C.

10. The method of claim 1 wherein the adding step includes conducting the olefin metathesis reaction from 1 minute to 24 hours.

11. The method of claim 1 wherein the adding step includes using the ruthenium complex of formula 1 in an amount of not more than 0.5 mol %.

12. The method of claim 1 wherein the adding step includes using the ruthenium complex of formula 1 in solid form and/or in the form of a solution in an organic solvent.

13. The method of claim 1 wherein the solution is solvent-free.

* * * * *